(12) United States Patent
Banks et al.

(10) Patent No.: US 6,440,689 B1
(45) Date of Patent: *Aug. 27, 2002

(54) MEASUREMENT OF MICROBIOLOGICAL ACTIVITY IN AN OPAQUE MEDIUM

(75) Inventors: Rodney H. Banks; Nancy L. Casselman, both of Aurora; Mita Chattoraj, Warrenville; Ronald V. Davis; Michael J. Fehr, both of Geneva; Sasireka S. Ramesh, Aurora; David P. Workman, Naperville, all of IL (US)

(73) Assignee: Ondeo Nalco Company, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/894,929

(22) Filed: Jun. 28, 2001

Related U.S. Application Data

(63) Continuation-in-part of application No. 09/475,585, filed on Dec. 30, 1999, now Pat. No. 6,329,165.

(51) Int. Cl.[7] .......................... C12Q 1/02; C12Q 1/00; G01N 33/53

(52) U.S. Cl. .............................. 435/29; 435/968; 435/4

(58) Field of Search ................. 435/29, 968, 4

(56) References Cited

U.S. PATENT DOCUMENTS

| | | | |
|---|---|---|---|
| 5,206,151 A | 4/1993 | Robertson | 435/29 |
| 5,336,600 A | 8/1994 | Monget | 435/34 |
| 5,413,916 A | 5/1995 | Anglin | 435/29 |
| 5,523,214 A | 6/1996 | Horn | 435/19 |
| 5,792,622 A | 8/1998 | Botsford | 435/29 |
| 6,060,318 A | 5/2000 | Moeggenborg et al. | 436/3 |
| 6,329,165 B1 * | 12/2001 | Chattoraj et al. | 435/29 |

OTHER PUBLICATIONS

D. Liu, and W.M.J. Strachan, Burlington, Characterization of microbial activity in sediment by reaszurin reduction, Arch. Hydrobiol. Beih. Ergebn. Limnol., 12, 1979, 24–31.

T. Ali–Vehmas, M. Louhi, and M. Sandholm, Automation of the Resazurin Reduction Test Using Fluorometry of Microtitration Trays, J. Vet. Med. B 38, 1991, 358–372.

B.W. Smith, B.T. Jones, and J.D. Winefordner, High–Precision Fluorimetry with a Light–Emitting Diode Source, Applied Spectroscopy, vol. 42, No. 8, pp. 1469–1472, 1988.

T. Ali–Vehmas, M. Louhi, and M. Sandholm, Automation of the Resazurin Reduction Test using Fluorometry of Microtitration Trays, J. Vet. Med. B 38, 1991, 358–372.

W. Fang, V. Myllys, and M. Sandholm, Resazurin reduction as a function of respiratory burst in bovine neutrophils, Am. J. Vet. Res., 58, 6, 1997, 601–607.

P.G. Nix, and M.M. Daykin, Resazurin Reduction Tests as an Estimate of Coliform and Heterotrophic Bacterial Numbers in Environmental Samples, Bull. Envrion. Contam. Toxicol., 49, 1992. 354–360.

(List continued on next page.)

Primary Examiner—Louise N. Leary
(74) Attorney, Agent, or Firm—Margaret M. Brumm; Thomas M. Breininger

(57) ABSTRACT

A method for monitoring the microbiological contamination of opaque media is described and claimed. In this method, a Fluorogenic Dye is added to an Aliquot of opaque medium. After a certain time period, a fluorometer capable of measuring fluorescent signals in an opaque medium is used to measure the fluorogenic signals of the Fluorogenic Dye and the Reacted Fluorogenic Dye. A Useful RATIO of the fluorescent signal of the Reacted Fluorogenic Dye to the fluorescent signal of the Fluorogenic Dye is calculated and the information gleaned from the RATIO is used to ascertain the state of microbiological contamination in the opaque medium.

26 Claims, 2 Drawing Sheets

OTHER PUBLICATIONS

Figure 1:
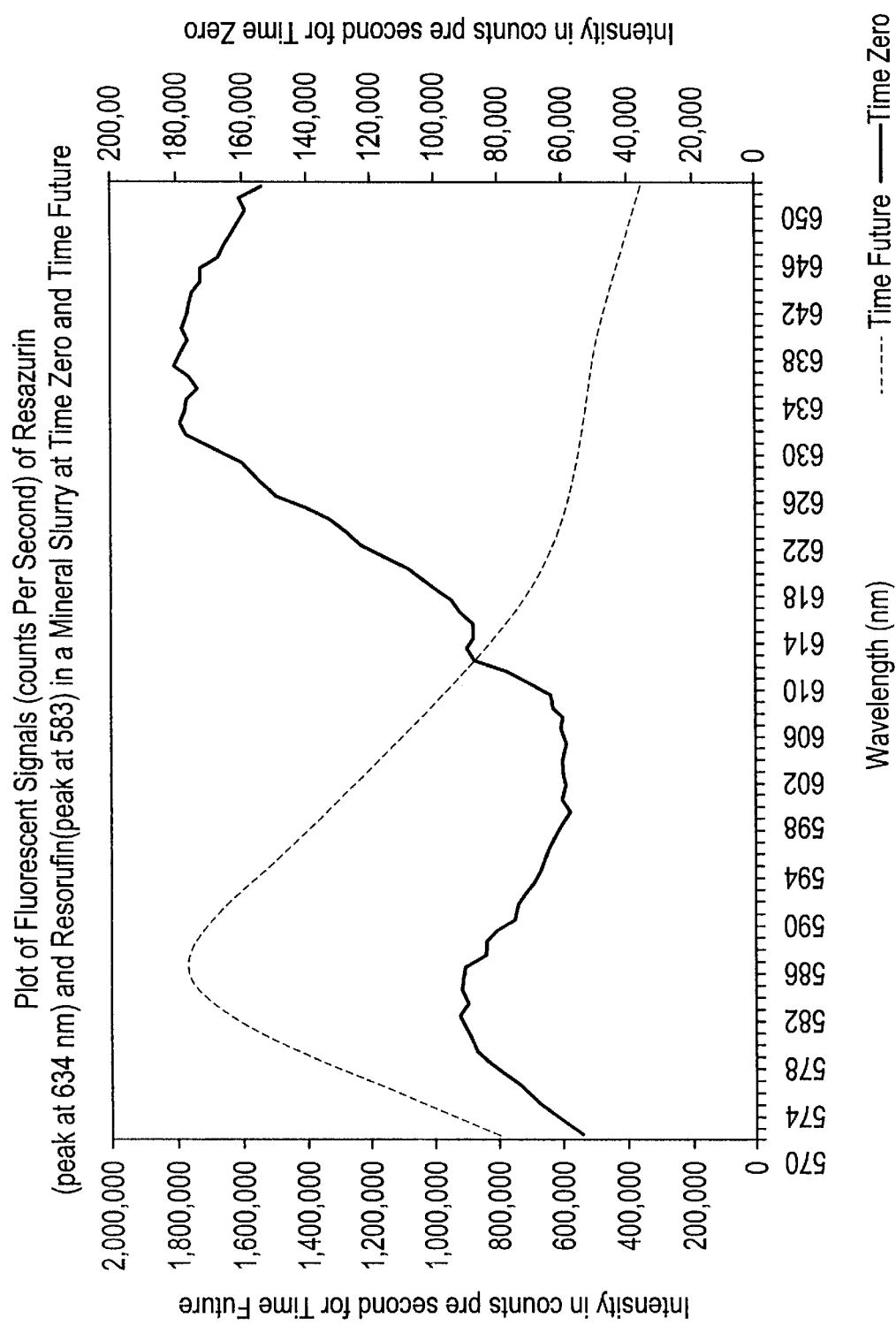

S. Gül, and D. Öztürk, Determination of Structure–Toxicity Relationship of Amphiprotic Compounds by Means of the Inhibition of the Dehydrogenase Activity of *Pseudomonas putida*, Turk J. Chem, 22, 1998, 341–349.

D. Liu, and W.M. J. Strachan, Measurement of microbial oxygen consumption in lake sediment, Canadian Research Nov.–Dec., 1977, 30–31.

D. Liu, and W.M.J. Strachan, A Field Method for Determining the Chemical and Biological Activity of Sediments, Water Research vol. 15, 1981, 353–359.

* cited by examiner

US 6,440,689 B1

MEASUREMENT OF MICROBIOLOGICAL ACTIVITY IN AN OPAQUE MEDIUM

CROSS-REFERENCE TO RELATED PATENT APPLICATION

This patent application is a continuation-in-part of U.S. patent application Ser. No. 09/475,585, "Measurement and Control Of Sessile and Planktonic Microbiological Activity In Industrial Water Systems", filed Dec. 30, 1999, now U.S. Pat. No. 6,329,165.

FIELD OF THE INVENTION

This invention is in the field of measurement of microbiological activity in highly scattering systems. Specifically, this patent application is in the field of fluorescent measurement of microbiological activity in opaque mediums such as slurries and colloids and certain Metal Working Fluids.

BACKGROUND OF THE INVENTION

Microbial contamination in opaque mediums such as slurries and colloids and certain Metal Working Fluids is a significant problem in many industries. In papermaking, additives such as kaolin slurry, precipitated calcium carbonate suspensions or starch solutions can harbor large microbial populations, which serve as inocullum for the papermnachine. Mining companies are required to supply industries such as paper and ceramics with treated and preserved additives and also need to monitor microbial contamination. Certain Metal Working Fluids are also susceptible to microbiological contamination.

The conventional method of controlling microbial growth is through the use of biocides. Biocides are chemicals that inhibit microbial growth by destroying the cell wall or cellular constituents of microorganisms. Physical conditions such as temperature, radiation, or interactions with treatment chemicals contained within a system can have a negative impact on the effectiveness of the biocide. To compensate for the reduced effect, biocides can either be added continuously or intermittently on an "as-required" basis. The minimal possible use of biocides is encouraged since biocides are both expensive and toxic. Thus, to prevent waste, constant monitoring and testing of the slurry or colloid or Metal Working Fluid is required to determine the proper quantity of biocide for controlling microbial growth.

Most slurries and colloids and certain Metal Working Fluids are opaque, which means they are not transparent to the passage of light. Another way to describe opaque media is that they are highly light scattering media. For the purposes of this patent application the term, "opaque" is used to refer to any medium which when placed in a 1 cm cuvette in the path of a non-absorbing visible light beam, acts to reduce the intensity of the light by 20% or more due to scattering.

When media are opaque, it is not possible to know what is inside an opaque media simply by looking at it. This means that it is impossible to tell if there is microbiological contamination of an opaque slurry or an opaque colloid or an opaque Metal Working Fluid by looking at it. Therefore, conventional, known optical methods of detection of microbiological contamination (such as optical density measurements and ATP measurements) cannot give results for opaque media. This is because light cannot pass through the sample, as light loss becomes inversely proportional to the extent of light scattering. Therefore, other methods of detecting microbial contamination in an opaque media must be used.

At present samples of opaque slurries or opaque colloids or opaque Metal Working Fluids are typically monitored for microbiological contamination using standard "plate-count" methods. Standard "plate-count" methods are typically referred to as "plating". Plating of samples requires trained personnel, equipment and a 48 hours incubation period during which microbes in the slurry can reproduce rampantly. The actual method of plate counting involves withdrawing a sample, diluting the sample, and applying the sample to the surface of a Nutrient agar medium. After incubation for 24 to 48 hours, the sample is checked for the presence of microorganisms and, where appropriate, the organisms are counted by manual or video means.

Some industrial situations require the use of High Pressure Liquid Chromatographs (HPLC) to determine if there is residual biocide left in the sample. HPLC can only measure biocide concentration and not microbial activity. HPLC also requires expensive equipment and trained personnel for routine measurements. Since HPLC only measures residual biocides, it cannot measure biocide resistant strains of microbiological organisms that are developing in the opaque media.

In addition to grab sampling, other on-site sampling techniques are available, such as Dip slide and Adenosine Triphosphate (ATP) tests. Unfortunately, such tests are not practical to use when measuring microbiological contamination in opaque medium because ATP tests require a transparent sample and therefore do not work in opaque medium and Dip slides require 24 to 48 hours for test results to develop. Thus, neither test is suitable for field evaluation of microbiological contamination.

Additional methods for monitoring the microbial populations in various mediums are described and claimed in the following references.

U.S. Pat. No. 5,206,151 describes and claims a method to measure the minimum inhibitory concentration of biocides by adding various amounts, types and combinations of biocides to aliquots of sample containing bacteria, adding an oxidation-reduction dye such as Resazurin or tetrazolium violet and Nutrients and monitoring the change in color.

U.S. Pat. No. 5,413,916 describes and claims a method for determination of toxicity of an environmental sample to bacteria by the addition of Resazurin and glutaraldehyde and bacteria to the sample and measuring absorbance (at 603 nm) as compared to a blank.

U.S. Pat. No. 5,336,600 describes and claims a method for detection of micro-organisms consisting of mixing a Resorufin (or Resorufin derivative not including Resazurin) and Nutrient medium and measuring a decrease in the fluorescence.

U.S. Pat. No. 5,523,214 describes and claims a method of identification of microbes using methylene blue and Resazurin stabilized with potassium ferricyanate or iron salts mixed with potassium ferrocyanate or sodium tungsate or tartrazine yellow or reactive red 4 or similar compounds. The patent claims substantial increase in sensitivity using this mixture as compared to using either dye alone.

Aliquots of sand filters were assessed using Resazurin reduction method, in an experiment described in an article entitled: "Resazurin reduction tests as an estimate of coliform and heterotrophic bacterial numbers in environmental samples" Can. Bull. Environ. Contam. Toxicol. 49, 354, 1992.

An article entitled, "Resazurin reduction as a function of respiratory burst in bovine neutrophils is an article in Am. J. Vet. Res. 58, 601, 1997, describes a technique of fluorometrically monitoring the end-point of Resazurin (Resorufin) as a measure of respiratory burst.

The article, "Automation of the Resazurin Reduction Test using Fluorometry of Microtitration Trays", by Ali-Vehmas, Louhi and Sandholm, *J. Vet. Med.,* B 38, 358–372 (1991) describes the automation of the fluorescent Resazurin-to-Resorufin reduction test for monitoring bacterial numbers in broth cultures and milk. The reduction of Resazurin (blue color) to Resorufin (a pink color) and finally and reversibly to dihydroresorufin (colorless) is well known in the art of determining mircrobiological contamination in milk. This method involves taking contaminated samples of milk in microtitration plates, adding a Nutrient medium and measuring the fluorescence corresponding to the Resorufin peak at 5 min intervals. This continuous measurement of the same sample makes this an automated measurement. The Resorufin intensity peaks when the increase in intensity due to conversion from Resazurin is offset by the decrease due to formation of the non-fluorescent dihydroresorufin. In this work, the sample population is increased significantly by addition of Nutrient medium (which is a necessary part of the method).

U.S. Pat. No. 6,060,318, entitled, "Tracing of Process Additives in Industrial Ceramics Applications", claims a fluorometric method for monitoring concentration of chemicals in ceramic slurries and powders having an external surface. In this patent, a solid-state fluorometer, (in the surface fluorescence configuration) is used to monitor the concentration of fluorescence molecules in ceramic slurries. Applications within ceramic slurries include monitoring of treatment dosages; measurement of mixing times in batch mixing vessels; determination of batch contamination from ball mills and other mixing vessels; and, efficiency of transfer from ball mills to mixing tanks.

It would be desirable to have an alternative method developed to determine the level of microbiological contamination in opaque slurries and opaque colloidal materials and opaque Metal Working Fluids.

SUMMARY OF THE INVENTION

The first aspect of the instant claimed invention is a process for monitoring of microbiological populations in an opaque medium comprising:

a) obtaining an Aliquot of material from the opaque medium;

b) adding a Fluorogenic Dye to said Aliquot, wherein said Aliquot is now referred to as Aliquot-Dye;

c) allowing said Fluorogenic Dye to react with any microbiological organisms present;

d) providing means for measurement of the fluorescent signals of the Fluorogenic Dye and the Reacted Fluorogenic Dye in said Aliquot-Dye;

e) using said means for measurement to measure the fluorescent signals of the Fluorogenic Dye and the Reacted Fluorogenic Dye, while discarding any measured fluorescent signal values below a predetermined noise level;

f) calculating the RATIO of the fluorescent signal of the Reacted Fluorogenic Dye to the fluorescent signal of the Fluorogenic Dye; and g) using said RATIO to monitor the extent of microbiological contamination in said opaque medium.

The second aspect of the instant claimed invention is the process of the first aspect of the instant claimed invention further comprising:

h) using said RATIO to determine the optimal amount of biocide to deliver to the opaque medium; and i) delivering said optimal amount of biocide to the opaque medium.

The third aspect of the instant claimed invention is a process for monitoring of microbiological populations in an opaque medium comprising:

(A) separating at least two Aliquots of material, optionally three Aliquots of material, from the opaque medium;

(B) adding nothing to the first Aliquot, wherein said first Aliquot is now referred to as Aliquot-Blank, adding a Fluorogenic Dye to the second Aliquot, wherein said second Aliquot is now referred to as Aliquot-Dye, and if the optional third Aliquot is present, adding a Metabolic Inhibitor to the optional third Aliquot, followed by adding Fluorogenic Dye to the optional third Aliquot, wherein said third Aliquot is now referred to as optional Aliquot-Inhibitor-Dye;

(C) allowing said Fluorogenic Dye to react with any microbiological organisms present;

(D) providing means for measurement of the fluorescent signals in said Aliquot-Blank, in said Aliquot-Dye, and in said optional Aliquot-Inhibitor-Dye, with the fluorescent signals being measured at the wavelength of the Fluorogenic Dye and at the wavelength of the Reacted Fluorogenic Dye;

(E) using said means for measurement of said fluorescent signals to measure the fluorescent signals in Aliquot-Blank, Aliquot-Dye, and in optional Aliquot-Inhibitor-Dye, at the wavelength of the Fluorogenic Dye and at the wavelength of the Reacted Fluorogenic Dye, while discarding any measured fluorescent signal values below a predetermined noise level;

(F) calculating the Useful RATIO, wherein the Useful RATIO is selected from the group consisting of RATIO of Adjusted for Background Fluorescence Fluorescent Signal of the Reacted Fluorogenic Dye to the Adjusted for Background Fluorescence Fluorescent Signal of the Fluorogenic Dye and RATIO of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye;

(G) using the Useful RATIO to monitor the extent of microbiological contamination in said opaque medium.

The fourth aspect of the instant claimed invention is the process of the third aspect of the instant claimed invention further comprising:

(H) using one or both of the Useful RATIOs from steps (F) and (G) to determine the optimal amount of biocide to deliver to said opaque medium; and (I) delivering said optimal amount of biocide to the opaque medium.

The fifth aspect of the instant claimed invention is a process for monitoring of microbiological populations in an opaque medium comprising:

a) obtaining an Aliquot of material from the opaque medium;

b) adding a Fluorogenic Dye into said Aliquot, wherein said Aliquot is now referred to as Aliquot-Dye;

c) allowing said Fluorogenic Dye to react with any microbiological organisms present for a time period known as Time Zero;

d) providing means for measurement of the fluorescent signals of the Fluorogenic Dye and the Reacted Fluorogenic Dye in said Aliquot-Dye;

e) using said means for measurement of said fluorescent signals to measure the fluorescent signals of the Fluorogenic Dye and the Reacted Fluorogenic Dye at Time Zero, while discarding any measured fluorescent signal values below a predetermined noise level;

f) calculating the RATIO of the fluorescent signal of the Reacted Fluorogenic Dye to the fluorescent signal of the Fluorogenic Dye and designating that RATIO the RATIO at Time Zero;

g) waiting for a time period, designated Time Future, h) measuring the fluorescent signals of the Fluorogenic Dye and the Reacted Fluorogenic Dye in Aliquot-Dye at Time Future;

i) calculating the RATIO of the fluorescent signal of the Reacted Fluorogenic Dye at Time Future to the fluorescent signal of the Fluorogenic Dye at Time Future, designating that RATIO the RATIO at Time Future;

j) comparing the RATIO at Time Future to the RATIO at Time Zero; and k) using the comparison of the RATIO at Time Future to the RATIO at Time Zero to monitor the extent of microbiological contamination in said opaque medium.

The sixth aspect of the instant claimed invention is the process of the fifth aspect of the instant claimed invention further comprising:

l) using the comparison of the RATIO at Time Future to the RATIO at Time Zero to determine the optimal amount of biocide to deliver to said opaque medium; and m) delivering said optimal amount of biocide to the opaque medium.

The seventh aspect of the instant claimed invention is a process for monitoring of microbiological populations in an opaque medium comprising:

(A) separating at least two Aliquots of material, optionally three Aliquots of material, from the opaque medium;

(B) adding nothing to the first Aliquot, wherein said first Aliquot is now referred to as Aliquot-Blank, adding a Fluorogenic Dye to the second Aliquot, wherein said second Aliquot is now referred to as Aliquot-Dye, and if the optional third Aliquot is present, adding a Metabolic Inhibitor followed by a Fluorogenic Dye to the optional third Aliquot, wherein the optional third Aliquot is now referred to as optional Aliquot-Inhibitor-Dye;

(C) allowing said Fluorogenic Dye to react with any microbiological organisms present for a time period known as Time Zero;

(D) providing means for measurement of the fluorescent signals in said Aliquot-Blank, in said Aliquot-Dye, and in said optional Aliquot-Inhibitor-Dye, with the fluorescent signals being measured at the wavelength of the Fluorogenic Dye and at the wavelength of the Reacted Fluorogenic Dye;

(E) using said means for measurement of said fluorescent signals to measure the fluorescent signals in Aliquot-Blank, Aliquot-Dye and in optional Aliquot-Inhibitor-Dye at Time Zero, at the wavelength of the Fluorogenic Dye and the wavelength of the Reacted Fluorogenic Dye, while discarding any measured fluorescent signal values below a predetermined noise level to yield fluorescent signals at Time Zero;

(F) calculating the Useful RATIO at Time Zero, wherein the Useful RATIO at Time Zero is selected from the group consisting of RATIO at Time Zero of the Adjusted for Background Fluorescence Fluorescent Signal of the Reacted Fluorogenic Dye to the Adjusted for Background Fluorescence Fluorescent Signal of the Fluorogenic Dye at Time Zero and optional RATIO of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye, (G) waiting for a time period, designated Time Future;

(H) using said means for measurement to measure the fluorescent signals at Time Future in Aliquot-Blank, Aliquot-Dye and in optional Aliquot-Inhibitor-Dye at the wavelength of the Fluorogenic Dye and the wavelength of the Reacted Fluorogenic Dye;

(I) calculating the Useful RATIO at Time Future, wherein the Useful RATIO at Time Future is selected from the group consisting of RATIO at Time Future of the Adjusted for Background Fluorescence Fluorescent Signal of the Reacted Fluorogenic Dye to the Adjusted for Background Fluorescence Fluorescent Signal of the Fluorogenic Dye at Time Future and optional RATIO at Time Future of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye;

(J) comparing the Useful RATIO at Time Future to the RATIO at Time Zero; and (K) using the comparison of the Useful RATIO at Time Future to the RATIO at Time Zero to monitor the extent of microbiological contamination in said opaque medium.

The eighth aspect of the instant claimed invention is the process of the seventh aspect of the instant claimed invention further comprising:

(L) using the comparison of the Useful RATIO at Time Future to the Useful RATIO at Time Zero to determine the optimal amount of biocide to deliver to said opaque medium; and (M) delivering said optimal amount of biocide to the opaque medium.

The ninth aspect of the instant claimed invention is a process for monitoring both active and inactive microbiological populations in an opaque medium, optionally accounting for chemical interference with the test method, as well as optionally accounting for background fluorescence comprising:

(A) obtaining two Aliquots of material, optionally three or four Aliquots of material from the opaque medium;

(B) adding a Fluorogenic Dye directly into the first Aliquot, wherein the first Aliquot is now referred to as Aliquot-Dye, adding Nutrient and Fluorogenic Dye to the second Aliquot, wherein the second Aliquot is now referred to as Aliquot-Nutrient-Dye, if the optional third Aliquot is present, adding a Metabolic Inhibitor and Fluorogenic Dye to the optional third Aliquot, wherein the optional third Aliquot is now referred to as optional Aliquot-Inhibitor-Dye, and if the optional fourth Aliquot is present, adding nothing to the fourth Aliquot, wherein the fourth Aliquot is now referred to as optional Aliquot-Blank;

(C) allowing said Fluorogenic Dye to react with any microbiological organisms present for a time period known as Time Zero;

(D) providing means for measurement of the fluorescent signals in said Aliquot-Dye, said Aliquot-Nutrient-Dye, said optional Aliquot-Inhibitor-Dye and in said optional Aliquot-Blank, with the fluorescent signals in each Aliquot being measured at the wavelength of the Fluorogenic Dye and the wavelength of the Reacted Fluorogenic Dye;

(E) using said means for measurement of said fluorescent signals to measure the fluorescent signals at Time Zero in said Aliquot-Dye, said Aliquot-Nutrient-Dye, said optional Aliquot-Inhibitor-Dye and in said optional Aliquot-Blank, at the wavelength of the Fluorogenic Dye and at the wavelength of the Reacted Fluorogenic Dye to yield fluorescent signals at Time Zero;

(F) calculating the Useful RATIO at Time Zero, wherein the Useful RATIO at Time Zero can be selected from the group consisting of RATIO at Time Zero of the Total Microbiological, Optionally Accounting for Interactions with chemicals and Optionally Accounting for Background Interferences Fluorescent Signal of the Reacted Fluorogenic Dye to the Total Microbiological, Optionally Accounting for Interactions with chemicals and Optionally Accounting for Background Interferences, Fluorescent Signal of the Fluorogenic Dye; the RATIO at Time Zero of the Active Microbiological Fluorescent Signal of the Reacted Fluorogenic Dye to the Active Microbiological Fluorescent Signal of the Fluorogemc Dye; and the RATIO at Time Zero of the Inactive Microbiological Fluorescent Signal of the Reacted Fluorescent Dye to the Inactive Microbiological Fluorescent Signal of the Fluorogenic Dye;

(G) waiting for a time period, designated Time Future, and measuring the fluorescent signals in said Aliquot-Dye, said Aliquot-Inhibitor-Dye, said optional Aliquot-Nutrient-Dye and said optional Aliquot-Blank at the wavelength of the Fluorogenic Dye and the Reacted Fluorogenic Dye at Time Future;

(H) calculating the Useful RATIO at Time Future, wherein the Useful RATIO at Time Future is selected from the group consisting of RATIO at Time Future of the Total Microbiological, Optionally Accounting for Interactions with chemicals and Optionally Accounting for Background Interferences Fluorescent Signal of the Reacted Fluorogenic Dye to the Total Microbiological, Optionally Accounting for Interactions with chemicals and Optionally Accounting for Background Interferences, Fluorescent Signal of the Fluorogenic Dye; the RATIO at Time Future of the Active Microbiological Fluorescent Signal of the Reacted Fluorogenic Dye to the Active Microbiological Fluorescent Signal of the Fluorogenic Dye and the RATIO at Time Future of the Inactive Microbiological Fluorescent Signal of the Reacted Fluorescent Dye to the Inactive Microbiological Fluorescent Signal of the Fluorogenic Dye;

(I) comparing the Useful RATIO at Time Future to the Useful RATIO at Time Zero; and (J) using the comparison of the Useful RATIO at Time Future to the Useful RATIO at Time Zero to monitor the extent of microbiological contamination in said opaque medium.

The tenth aspect of the instant claimed invention is the process of the ninth aspect of the instant claimed invention further comprising:

(K) using said comparison of the Useful RATIO at Time Future to the Useful RATIO at Time Zero to determine the optimal amount of biocide to deliver to said opaque medium; and (L) delivering said optimal amount of biocide to the opaque medium.

DETAILED DESCRIPTION OF THE DRAWINGS

FIG. 1 shows a plot of fluorescent signals (in counts per second) of Resazurin and Resorufin in a Mineral Slurry at Time Zero and at Time Future. The spectra shown in FIG. 1 were obtained using a SPEX™ fluorometer available from Jobin Yvon Spex, 3880 Park Avenue, Edison N.J. 08820. The SPEX™ fluorometer uses single photon counting so the readings are reported in counts per second. In FIG. 1, the Time Zero spectrum is shown as the smooth line and the y-axis for the Time Zero spectrum is the secondary y-axis with units of from 0 to 200,000 counts per second. The Time Future spectrum in FIG. 1 is shown as the dotted line and the y-axis for the Time Future spectrum is the primary y-axis with units of from 0 to 2,000,000 counts per second.

Figure 2:
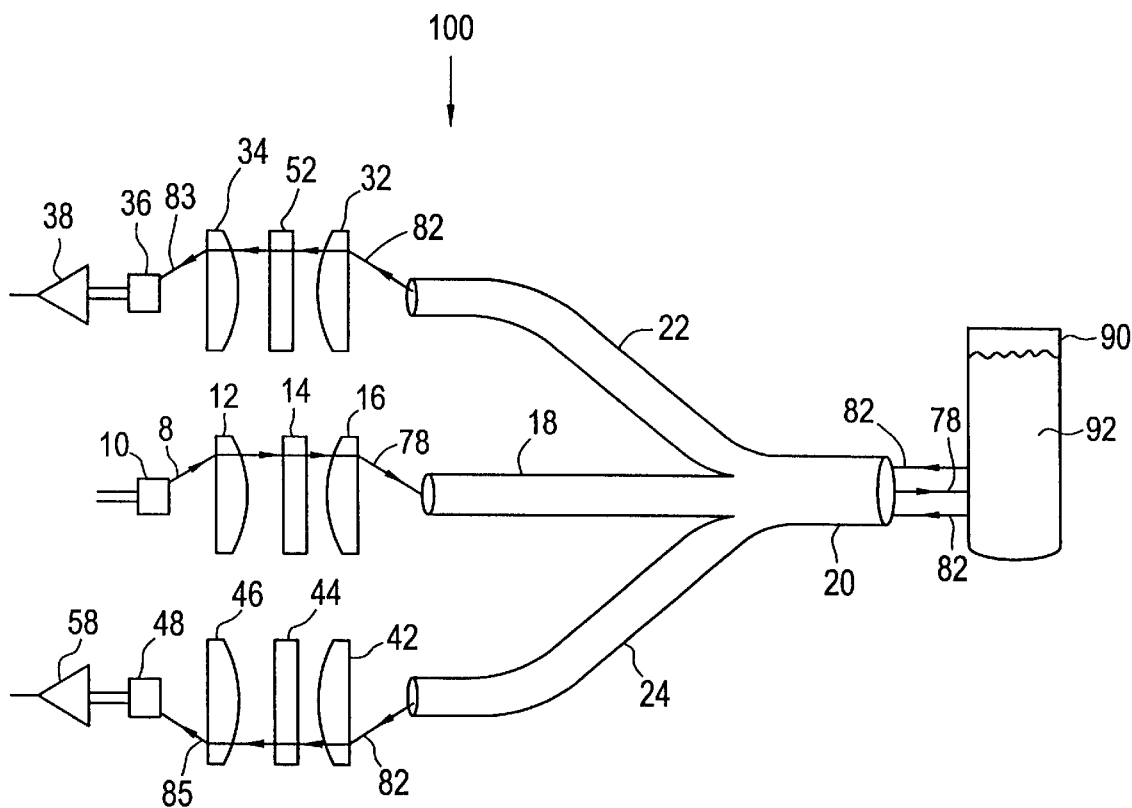

FIG. 2 shows a Front-Face Fluorometer. (Not claimed.)

DETAILED DESCRIPTION OF THE PREFERRED EMBODIMENTS

Throughout this patent application the following terms have the indicated meanings.

Aldrich refers to ALDRICH®, P.O. Box 355, Milwaukee, Wis. 53201, USA, telephone numbers (414) 273-3850 or (900) 962-9591)).

A "colloid" is an opaque liquid containing submicroscopic particles that do not settle out. "Isotropic" refers to the fact that if a moiety is considered a point source, and excitation light is directed at the moiety, fluorescent light is emitted equally over $2\pi$ steradians, creating, in effect, a sphere in 3 dimensions. Because of the isotropic distribution of fluorescent light, in practice, collection of the fluorescent light signal usually occurs at 90° relative to the excitation (photon) source to minimize the photons (light) collected that are attributed to the excitation (photon) source. This also helps to minimize light scattering.

Nalco refers to ONDEO Nalco Company, ONDEO Nalco Center, 1601 W. Diehl Road, Naperville, Ill. 60563, USA, (630) 305-1000.

"nm" means nanometers; which are $10^{-9}$ meters.

A "slurry" is an opaque suspension, usually aqueous; made by mixing an insoluble substance, such as cement or clay, with enough water or other liquid to allow the mixture to flow viscously.

The first aspect of the instant claimed invention is a process for monitoring of microbiological populations in an opaque medium comprising:

a) obtaining an Aliquot of material from the opaque medium;

b) adding a Fluorogenic Dye to said Aliquot, wherein said Aliquot is now referred to as Aliquot-Dye;

c) allowing said Fluorogenic Dye to react with any microbiological organisms present;

d) providing means for measurement of the fluorescent signals of the Fluorogenic Dye and the Reacted Fluorogenic Dye in said Aliquot-Dye;

e) using said means for measurement to measure the fluorescent signals of the Fluorogenic Dye and the Reacted Fluorogenic Dye, while discarding any measured fluorescent signal values below a predetermined noise level;

f) calculating the RATIO of the fluorescent signal of the Reacted Fluorogenic Dye to the fluorescent signal of the Fluorogenic Dye; and g) using said RATIO to monitor the extent of microbiological contamination in said opaque medium.

The second aspect of the instant claimed invention is the process of the first aspect of the instant claimed invention further comprising:

h) using said RATIO to determine the optimal amount of biocide to deliver to the opaque medium; and i) delivering said optimal amount of biocide to the opaque medium.

Initially, an Aliquot of material is removed from an opaque medium. For purposes of this invention the opaque medium is selected from the group consisting of opaque slurries, opaque colloids and opaque Metal Working Fluids. Slurries and colloids suitable for testing in this way include slurries and colloids used in industry. Specific slurries and colloids and Metal Working Fluids capable of being tested by the method of the instant claimed invention include those used in the mineral processing industry, those used in the pulp and paper industry, those used in the ceramics industry, those used in the coatings industry and any other slurry or colloid or Metal Working Fluid used in an industrial process that is not an industrial process in the food or beverage industry.

Opaque slurries and opaque colloids used in the mineral industry include clay mineral slurries (kaolin), calcium sulfate slurries, calcium carbonate slurries, coal fines slurries and ore slurries from metal mining operations (such as copper, gold, molybdenum, iron, aluminum and nickel).

Opaque slurries and opaque colloids used in the pulp and paper industry include polymer solutions, starch slurries (aka starch "solutions") and mineral slurries such as kaolin slurries and precipitated calcium carbonate suspensions.

Opaque slurries used in ceramic processing include mineral slurries such as clay based systems and metal oxides and some polymer solutions.

Metal Working fluids are chemical mixtures used to reduce friction, and heat at the point of contact between a workpiece and a worktool. In addition, Metal Working Fluids provide wear protection to the worktool and as well as corrosion protection to machines and workpiece. They are also formulated to have other desirable properties depending on the application including but not limited to: resistance to microbiological fouling, antifoam, and low misting. Metal Working Fluids in operation are highly scattering systems due to contamination by other fluids or are designed to be highly scattering oil in water emulsions.

The method of the instant claimed invention should be applicable to all the water extendable Metal Working Fluids i.e. synthetic, semi-synthetics, and soluble oil Metal Working Fluids. All these fluids can and often are subject to microbiological contamination.

A Fluorogenic Dye compound is added to the Aliquot to be tested and monitored.

The measured Fluorogenic Dye response will be a sum total of the response of microbiological organisms in the Aliquot containing the Fluorogenic Dye. When using Aliquot sampling it is possible, though not required, to take Aliquots from several different locations within the slurry or colloid in order to obtain the averaged microbiological organism activity of the system.

The Fluorogenic Dye compound added to the Aliquot must be a molecule that undergoes a substantial change in its fluorescent signal on interaction with a broad population of microbiological organisms. Therefore, Fluorogenic Dyes suitable for use in the instant claimed process must have a detectable fluorescent signal prior to their reacting with microorganism and also must have a different fluorescent signal after they have reacted with microorganisms.

Suitable Fluorogenic Dyes, include, but are not limited to, acetic acid ester of pyrene 3,6,8-trisulfonic acid;

carboxyfluorescein diacetate, 9H-(1,3-dichloro-9,0-dimethylacridine-2-one-7-yl), D-glucuronide;

9H-(1,3-dichloro-9,9-dimethylacridin-2-one-7-yl);

Resorufin β-D-galactopyranoside;

fluorescein di-β-D-galactopyranoside;

fluorescein di-β-D-glucuronide;

Resorufin β-D-glucuronide;

fluorescein diphosphate;

7-hydroxy-3H-phenoxazin-3-one 10-oxide (hereinafter "Resazurin");

7-hydroxy-3H-phenoxazin-3-one 10-oxide, sodium salt (hereinafter "Resazurin, sodium salt");

methylene blue;

pyranine phosphate;

pyrene 3,6,8-trisulfonic acid 1-phosphate; and salts therof.

The preferred Fluorogenic Dye is Resazurin.

All of these Fluorogenic Dyes are either commercially available (for example, Resazurin is available as Resazurin, sodium salt, from Aldrich) or, as is the case with pyranine phosphate, these Fluorogenic Dyes are capable of being synthesized using procedures reported in the literature.

After the Fluorogenic Dye is added to the Aliquot, the Aliquot is optionally stirred to mix the dye throughout the Aliquot.

Typically, the opaque medium, either a slurry or colloid or Metal Working Fluid contains some type of microbiological organisms. In any slurry or colloid or Metal Working Fluid used in an industrial process there are expected to be colonies of microbiological organisms in different areas. The level of microbial activity in each of these slurries or colloids is a function of different factors including initial population of microbiological organisms, aeration, temperature, water flow, the presence of microbial Nutrients and the removal of microbial waste.

In order to allow sufficient time to pass such that the Fluorogenic Dye reacts with the microorganisms present, it is recommended to wait at least about 1 minute, preferably at least about 5 minutes, more preferred to wait at least about 240 minutes and most preferred to wait at least about 480 minutes, after adding the Fluorogenic Dye before using the fluorometer to measure the fluorometric signals. In the method of the first, second, third and fourth aspects of the invention only one measurement of fluorescent signals is done. Thus, for those aspects of this invention, this time period is the only time period for the measurement.

In the fifth, sixth, seventh, eighth, ninth and tenth aspects of the instant claimed invention the time period before the first measurements of fluorescent signal is that time period referred to as Time Zero. Time Zero is at least about 1 minute, preferably at least about 5 minutes, more preferred to wait at least about 20 minutes and most preferred to wait at least about 30 minutes, after adding the Fluorogenic Dye before using the fluorometer to measure the fluorometric signals.

In the fifth, sixth, seventh, eighth, ninth and tenth aspects of the invention, Time Future is the time at least about 4 hours after Time Zero, preferably it is the time at least about 6 hours after Time Zero, and more preferably, Time Future is at least about 8 hours after Time Zero.

The Fluorogenic Dye must be added to the Aliquot in an effective amount such that it is capable of determining microbe activity. An effective amount of Fluorogenic Dye is between about 0.5 ppm and about 200 ppm, preferably between about 1 ppm and about 50 ppm, most preferably between about 10 ppm and about 30 ppm, and the most highly preferable amount of Fluorogenic Dye added is about 25 ppm. When the salt form of the dye, such as Resazurin, sodium salt, is added to the industrial water system, the calculation of ppm is based on the active amount of the Fluorogenic Dye present.

Of course, the amount the amount of Fluorogenic Dye used may be greater than these preferred amounts. It is believed without intending to be bound thereby that amounts greater than 200 ppm will waste Fluorogenic Dye without providing a commensurate benefit to the measurement of microbial activity. Additional factors influencing dye addition to the system include the type of dye and the type of fluids contained within the slurry or colloid or Metal Working Fluid.

The fluorometer can be used to measure the fluorescent signals of both the Fluorogenic Dye and the Reacted Fluorogenic Dye.

Commercially available fluorometers include those available from Nalco, including, but not limited to, the TRASAR® 700 fluorometer with sample cuvette position modified so that it is read using a "grazing angle" fluorescence measuring technique useful for opaque media such as slurries, colloids and Metal Working Fluids.

A SPEX™ fluorometer, available from Jobin Yvon SPEX, 3880 Park Avenue, Edison N.J. 08820, fitted with either:

(1) a solid sample support that allows collection of fluorescence from the front face of the cell or (2) a bifurcated fiber optic cable that allows light of the desired wavelength to impinge upon the sample and allows for collection and transmission of the emission back to the detection system; can be used to perform fluorescence measurements in opaque samples.

Another type of fluorometer suitable for use in the method of the instant claimed invention is described and claimed in U.S. patent application Ser. No. 09/893,831, entitled "Mirror Fluorometer", filed Jun. 28, 2001.

Another type of fluorometer suitable for use in the method of the instant claimed invention is known as a Front-Face Fluorometer. A Front-Face Fluorometer is illustrated in FIG. 2. Referring to FIG. 2, Front-Face Fluorometer 100 uses a light source 10 which projects emitted light 8 through first lens 12, and excitation filter 14, and second lens 16. First lens 12 is an aspheric lens. Second lens 16 could be either an aspheric lens or a PCX lens. Light of a selected frequency emerges from second lens 16 as excitation light 78. Excitation light 78 enters into first arm 18 of trifurcated fiber optic cable 20 and from there into sample tube 90 containing Aliquot 92. Aliquot 92 contains either an Aliquot from an opaque slurry or an opaque colloid or an opaque Metal Working Fluid to which Fluorogenic Dye and optionally Metabolic Inhibitor and optional Nutrient has been added. Alternatively, Aliquot 92 may not contain any Fluorogenic Dye, or Metabolic Inhibitor or Nutrient. In that case, Aliquot 92 is referred to as Aliquot-Blank.

Preferably, Fluorogenic Dye is chosen such that one wavelength of Excitation light is able to excite both Fluorogenic Dye and Reacted Fluorogenic Dye. Preferably, Fluorogenic Dye is Resazurin which is excited by Excitation Light at wavelength 550 nm. Both Resazurin (Fluorogenic Dye) and Resorufin (Reacted Fluorogenic Dye) are excited by Excitation Light at wavelength 550 nm using a SPEX™ fluorometer. Flurophores in Aliquot 92 send emitted light 82 back through second arm 22 and third arm 24 of trifurcated fiber optic cable 20.

Emitted light 82 travels through first PCX lens 32, first emission filter 52 and second PCX lens 34 and emerges from second PCX lens 34 as First emitted fluorescent signal 83. First emitted fluorescent signal 83 is emitted fluorescent light with a specific wavelength. The way that the desired wavelength of light for first emitted fluorescent signal 83 is obtained, is by first determining what wavelength of fluorescent light needs to be detected (as first emitted fluorescent signal 83) in order to conduct the method of the instant claimed invention, and then selecting PCX lens 32, first emission filter 52 and second PCX lens 34 such that the desired wavelength of light for first emitted fluorescent signal 83 emerges from second PCX lens 34. First emitted fluorescent signal 83 enters into first photodiode 36. First optional amplifier 38 is used to amplify First emitted fluorescent signal 83 to make the signal more detectable.

Emitted light 82 travels through third arm 24 of trifurcated fiber optic cable 20, through third PCX lens 42, second emission filter 44 and fourth PCX lens 46 and emerges from fourth PCX lens 46 as second emitted fluorescent signal 85. Second emitted fluorescent signal 85 is fluorescent light with a specific wavelength. The way that the desired wavelength of second emitted fluorescent signal 85 is obtained, is by first determining what wavelength of fluorescent light needs to be detected (as second emitted fluorescent signal 85) in order to conduct the method of the instant claimed invention, and then selecting third PCX lens 42, second emission filter 44 and fourth PCX lens 46 such that the desired wavelength of light for second emitted fluorescent signal 85 emerges from fourth PCX lens 46. Second emitted fluorescent signal 85 enters into second photodiode 48. Second optional amplifier 58 is used to amplify second emitted fluorescent signal 85 to make the signal more detectable.

Light source 10 may be a light emitting diode or a laser or a filament based lamp or a flashlamp. Light source 10 is preferably a light emitting diode. Suitable light emitting diodes (green LED, emits light at 525 nm, part no. NSPG-500S) are available from Nichia America Corporation, 3775 Hempland Road, Mountville, Pa. 17554, (717) 285-2323.

PCX lenses (Part No. L45-437) and Aspheric lenses are available from Edmund Industrial Optics, 101 East Gloucester Pike, Barrington, N.J. 08007 (800) 363-1992.

Amplifiers (part no. AFC 2101) are preferably dual current integrators from Burr-Brown, 6730 S. Tucson Blvd., Tucson, Ariz. 85706 (520) 746-1111.

The photodiode (part no. S2386-5K) is available from Hamamatsu, 360 Foothill Road, Bridgewater, N.J. 08807 (908) 231-0960.

Excitation filter (part no. 535DF35) and Emission filters (part no. 635DF55) are available from Omega Optical, P.O. Box 573, Brattleboro, Vt. 05302 (802) 254-2690.

Trifurcated Fiber Optic Cable is available from Dolan-Jenner Industries, 678 Andover Street, Lawrence, Mass. 01843 (978) 681-8000.

The preferred fluorometer for use in the Method of the Instant Claimed Invention is the Front-Face Fluorometer.

Measuring the fluorescent signal of both the Fluorogenic Dye and the Reacted Fluorogenic Dye is a known procedure to someone skilled in the art of fluorometry. To use any of the above described fluorometers to detect the fluorescent signal of a Fluorogenic Dye and a Reacted Fluorogenic Dye means that the fluorometer must be capable of supplying the requisite wavelength of excitation light and also must be capable of detecting the requisite wavelength of emitted light. As stated previously, Resazurin (Fluorogenic Dye) and Resorufin (Reacted Fluorogenic Dye) are both excited using light with a wavelength of from about 532 nm to about 550nm and the emission fluorescent signals for each compound are detected and measured at 583 nm and 634 nm (corresponding to Resorufin and Resazurin respectively).

One of the reasons that Resazurin is the preferred Fluorogenic Dye is because both Resazurin (Fluorogenic Dye) and Resorufin (Reacted Fluorogenic Dye) are excited by light at the same wavelength. It is of course possible to conduct the instant claimed method using a Fluorogenic Dye that is excited by light of a different wavelength, as compared to the light used to excite the Reacted Fluorogenic Dye. For those fluorometers capable of emitting light at only one wavelength and/or detecting only one fluorescent signal at the emitted light wavelength, more than one fluorometer must be used; with one fluorometer being used to detect the fluorescent signal of the Fluorogenic Dye and the other being used to detect the fluorescent signal of the Reacted Fluorogenic Dye.

In the first aspect of the instant claimed invention the RATIO of the fluorescent signal of the Fluorogenic Dye to the fluorescent signal of the Reacted Fluorogenic Dye is depicted as follows:

$$\text{RATIO} = \frac{\text{fluorescent signal of Reacted Fluorogenic Dye}}{\text{fluorescent signal of Fluorogenic Dye}}$$

By taking a ratio of Reacted Fluorogenic Dye to Fluorogenic Dye, the signal loss due to scattering of light is factored out because the amount of light loss is proportional to the opacity of the Aliquot.

The RATIO is a unitless number. The RATIO can be calculated manually or with a calculator or with a computer program. In practice the RATIO be calculated using an appropriate computer program such that a record of the RATIO can be continuously calculated at set intervals. The absolute value of the Ratio (the first, second, third and fourth aspects of the invention) or the rate of change of the RATIO (the fifth, sixth, seventh, eighth, ninth and tenth aspects of the invention) can then be used to determine the level of microbiological activity in the opaque medium.

Computer programs can be written to automatically calculate the RATIO. A person with ordinary skill in the art of writing computer programs would know how to write a computer program that would automatically calculate the RATIO.

Regardless of how the RATIO is being calculated, an operating system can be created out of commercially available components that can be programmed to process the RATIO. This operating system can use the RATIO to operate the controls that physically add biocide to the opaque medium. The computing means within the operating system can be any digital computer such as, but not limited to, a Programmable Logic Controller (PLC), personal computer or other computing device. The biocide feeder can be a simple container for holding a liquefied biocide and a pump. Preferably the pump is capable of delivering a measured amount of biocide to the slurry or colloid and can be activated manually or by a signal from the computing device to deliver such measured amount.

Regarding the rate of change of the RATIO, it is known that in the absence of biocide, if the RATIO increases, then the level of microbiological activity is increasing.

When the method of the instant claimed invention is conducted in the presence of biocides certain adjustments have to be made. People of ordinary skill in the art know what biocides are used in opaque media. Biocides added in response to unacceptable levels of microbial activity include oxidizing and non-oxidizing biocides.

Oxidizing biocides include, but are not limited to:

BCDMH (92.5%, 93.5%, 98%), which is either 1,3-dichloro-5,5-dimethylhydantoin and 1-bromo-3-chloro-5,5-dimethylhydantoin (CAS Registry No. 16079-88-2) or a mixture thereof;

bleaches, including stabilized bleaches;

bromine, including stabilized bromine;

calcium hypochlorite (CAS Registry No. 7778-54-3) "Cal Hypo" (68%);

chlorine, including stabilized chlorine (8.34%);

$H_2O_2$/PAA (21.7%/5.1%) which is hydrogen peroxide (CAS Registry No. 7722-84-1)/peracetic acid (CAS Registry No. 79-21-0);

hypobromite;

hypobromous acid;

iodine;

organobromines;

NaBr (42.8%, 43%, 46%) which is sodium bromide;

NaOCl (10%, 12.5%) which is sodium hypochlorite (CAS Registry No. 7681-52-9);

and mixtures thereof.

Non-oxidizing biocides include, but are not limited to,

Adamantane is 67.5 wt. % 1-(3-chloroallyl)-3,5,7-Triaza-1-Azoniaadamantane chloride (CAS Reg. No. 4080-31-3);

ADBAC Quat (10%, 40%(CAS Registry No. 68391-0-5), 80%) which is alkyl dimethyl benzyl ammonium chloride, also known as "quat";

ADBAC quat(15%)/TBTO (tributyl tin oxide) 5%;

ADBAC(12.5%)/TBTO (2.5%) which is ADBAC Quat/ bis tributyl tin oxide (CAS Registry No. 56-35-9);

Bronopol is 10 wt. % 2-Bromo-2-Nitro-1,3-Propanediol (CAS Reg. No. 52-51-7);

carbamates (30%), of formula $T_2NCO_2H$, where $T_2$ is a $C_1$–$C_{10}$ alkyl group;

copper sulfate (80%);

DBNPA (20%, 40%), which is 2,2-dibromo-3-nitrilopropionamide (CAS Registry No. 10222-01-2);

DDAC Quat (50%) which is didecyl dimethyl ammonium chloride quat;

DPEEDBAC Quat (1%) which is (2-(2-p-(diisobutyl) phenoxy)ethoxy)ethyl dimethyl, dimethyl benzyl;

glutaraldehyde (15%, 45%) (CAS Registry No. 111-30-8);

glutaraldehyde (14%)/ADBAC quat (2.5%);

HHTHT which is hexahydro-1,3,5-tris (2-hydroxyethyl)-5-triazine (78.5%);

isothiazolones (1.5%, 5.6%) which are a mixture of 5-chloro-2-methyl-4-isothiazoline-3-one (CAS Registry No. 26172-55-4) and 2-methyl-4-isothiazoline-3-one (CAS Registry No. 2682-20-4);

MBT (10%) which is 10–20 wt. % Methylene bis thiocyanate (CAS Reg. No. 6317-18-6) and 5–10 wt. % Ethoxylated phenol (CAS Reg. No. 41928-09-0);

polyquat (20%, 60%), a polymeric quaternary compound; polyamines and salts thereof--polymeric amine compounds;

terbutylazine (4%, 44.7%) which is 2-(tert-butylamino)-4-chloro-6-ethylamino-5-triazine (CAS Registry No. 5915-41-3);

thione is 24 wt % 3,5-dimethyl-1,3,5,2H tetrahydrothiadiazine-2-thione (CAS Reg. No. 533-74-4) and 1–5 wt % sodium hydroxide (CAS Reg. No. 1310-73-2);

TMTT (24%)--tetramethylthiuram disulfide;
and mixtures thereof.

Any combination of the above biocides may be used. Additional biocides may also be used. These additional biocides would include those known to a person of ordinary skill in the art of biocides. The only restriction on choice of biocide is that if the biocide reacts with the Fluorogenic Dye faster that it reacts with (destroys) the microbes, then it would be unacceptable.

It has been found that all of the Fluorogenic Dyes suitable for use in the instant claimed invention are susceptible to degradation (aka "quenching") of varying degrees in the presence of oxidizing biocides. When the method of the instant claimed invention is used in an opaque medium where these oxidizing biocides are present it is important to remove the Aliquot(s) from the opaque medium at a point that is as far as possible away from the point where the oxidizing biocide is added to the slurry or colloid or Metal Working Fluid.

In the presence of oxidizing biocides, the method of the instant claimed invention must take into account this quenching phenomenon, by not considering any fluorescent signals, unless they quantified above a certain minimum "noise" level. This minimum "noise" level can be determined with reasonable certainty for every slurry and colloid and Metal Working Fluid where the method of the instant claimed invention can be practiced by a person of ordinary skill in the art of fluorometry.

Even without the presence of oxidizing biocide, it is necessary to discard any fluorescent signals that are not above a "minimum noise level" for the system. This "minimum noise level" will be different for each opaque medium. A person of ordinary skill in the art of fluorometry can determine the "minimum noise level" for each opaque medium.

This quenching phenomena can also be observed with non-oxidizing biocides, chemical reducing substances (such as sulfites) and acidic pH, because each of these compounds/phenomena react to reduce the Fluorescent signal of the Fluorogenic Dye. This quenching of the signal of the Fluorogenic Dye can be accounted for by using a Metabolic Inhibitor as well as a Fluorogenic Dye in an Aliquot. Using a Metabolic Inhibitor in one Aliquot to suppress the microbiological reduction of Fluorogenic Dye enables the differentiation of the chemical and biological reductions of the Fluorogenic Dyes. In this way it is possible to determine the amount of reduction attributable to microbiological activity separate from the amount of reduction attributable to chemical reduction.

The Aliquot, referred to as Aliquot-Inhibitor-Dye, will show only the change in the fluorescent signal of the Fluorogenic Dye attributed to Interactions with chemicals, because the Metabolic Inhibitor stops the microbiological activity which means the microbiological activity is not able to affect the Fluorogenic Dye.

By calculating the RATIO as opposed to simply measuring an absolute value of fluorescent signals information is obtained that is (1) independent of Fluorogenic Dye concentration and (2) more sensitive to the microbial activity. The sensitivity is due to the fact that the microbiological organisms convert Fluorogenic Dye to Reacted Fluorogenic Dye with the RATIO increase being due to both the decrease in the fluorescent signal of the Fluorogenic Dye and increase in the fluorescent signal of the Reacted Fluorogenic Dye. RATIO is also required due to differences in scattering and background fluorescence of various samples of slurries that would otherwise introduce errors to absolute value measurements.

Microbiological organisms commonly found within a slurry or colloid or Metal Working Fluid which thus far have been detectable by and responding to the detection methods of the present process include, but are not limited to, Pseudomonas, Bacillus, Klebsiella, Enterobac, Escherichia, Sphaerotilus, Haliscomenobacter. As mentioned previously this listing is not exhaustive, noting that other bacteria and/or microorganisms may be detectable by the process using said apparatus.

The third aspect of the instant claimed invention is a process for monitoring of microbiological populations in an opaque medium comprising:

(A) separating at least two Aliquots of material, optionally three Aliquots of material, from the opaque medium;

(B) adding nothing to the first Aliquot, wherein said first Aliquot is now referred to as Aliquot-Blank, adding a Fluorogenic Dye to the second Aliquot, wherein said second Aliquot is now referred to as Aliquot-Dye, and if the optional third Aliquot is present, adding a Metabolic Inhibitor to the optional third Aliquot, followed by adding Fluorogenic Dye to the optional third Aliquot, wherein said third Aliquot is now referred to as optional Aliquot-Inhibitor-Dye;

(C) allowing said Fluorogenic Dye to react with any microbiological organisms present;

(D) providing means for measurement of the fluorescent signals in said Aliquot-Blank, in said Aliquot-Dye, and in said optional Aliquot-Inhibitor-Dye, with the fluorescent signals being measured at the wavelength of the Fluorogenic Dye and at the wavelength of the Reacted Fluorogenic Dye;

(E) using said means for measurement of said fluorescent signals to measure the fluorescent signals in Aliquot-Blank, Aliquot-Dye, and in optional Aliquot-Inhibitor-Dye, at the wavelength of the Fluorogenic Dye and at the wavelength of the Reacted Fluorogenic Dye, while discarding any measured fluorescent signal values below a predetermined noise level;

(F) calculating the Useful RATIO, wherein the Useful RATIO is selected from the group consisting of RATIO of Adjusted for Background Fluorescence Fluorescent Signal of the Reacted Fluorogenic Dye to the Adjusted for Background Fluorescence Fluorescent Signal of the Fluorogenic Dye and RATIO of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye;

(G) using the Useful RATIO to monitor the extent of microbiological contamination in said opaque medium.

The fourth aspect of the instant claimed invention is the process of the third aspect of the instant claimed invention further comprising:

(H) using one or both of the Useful RATIOs from steps (F) and (G) to determine the optimal amount of biocide to deliver to said opaque medium; and (I) delivering said optimal amount of biocide to the opaque medium.

In these third and fourth aspects, a second Aliquot of opaque medium is taken for analysis. This Aliquot is referred to as Aliquot-Blank. No Fluorogenic Dye is added to Aliquot Blank. A fluorometer is used to measure the fluorescent signals at the wavelength of the Fluorogenic Dye and the Reacted Fluorogenic Dye in Aliquot-Blank. The fluorescent signals at the wavelength of the Fluorogenic Dye and the Reacted Fluorogenic Dye in Aliquot-Blank are subtracted from the fluorescent signal of the Fluorogenic Dye and the Reacted Fluorogenic Dye in Aliquot-Dye, prior to calculation of the RATIO. Use of Aliquot-Blank accounts for the background fluorescence at the wavelength of the Fluorogenic Dye and the Reacted Fluorogenic Dye that exists in the opaque medium, prior to the addition of Fluorogenic Dye.

Note that in the seventh, eighth, ninth and tenth aspect of the instant claimed invention it is specified that the fluorescent signals of Aliquot-Blank be measured at both Time Zero and at Time Future. In practice, it is not always required to take another measurement of the fluorescent signals in Aliquot-Blank at Time Future; instead, the fluorescent signals from Aliquot-Blank at Time Zero are used in both the RATIO at Time Zero calculations and the RATIO at Time Future calculations.

Also in the third and fourth aspects of the instant claimed invention, optionally a third Aliquot of opaque medium is removed. When this third Aliquot is taken, a Metabolic Inhibitor is added to the third Aliquot, followed by addition of the Fluorogenic Dye. This Aliquot is now referred to as Aliquot-Inhibitor-Dye.

Suitable Metabolic Inhibitors are selected from the group consisting of halogenated phenols including, but not limited to, pentachlorophenol and cresol isomers. The preferred Metabolic Inhibitor is a solution of pentachlorophenol in dipropylene glycol methyl ether. The amount of Metabolic Inhibitor added to the Aliquot is from about 100 ppm to about 20,000 ppm, preferably from about 1000 ppm to about 10,000 ppm and most preferably is about 5000 ppm.

As mentioned previously, the fluorescent signals of Aliquot-Inhibitor-Dye are those signals showing the interaction of Fluorogenic Dye with chemicals in the opaque medium separate from the interaction of Fluorogenic Dye with microbiological organisms in the opaque medium. If necessary or desirable, the signal of Aliquot-Blank is subtracted from the signal of Aliquot-Inhibitor-Dye and also is subtracted form Aliquot-Dye to yield the Fluorescent signals where the Fluorescent Signals have been modified to account for Interactions with chemicals and Background fluorescence.

Thus the RATIOs calculated in the third and fourth aspects of the invention can account for Background Fluorescence and optionally account for Chemical Interference.

The methods of the fifth, sixth, seventh, eighth, ninth and tenth aspect of the instant claimed invention require a pair of measurements to be done. The first set of measurements is done at Time Zero and the second set of Measurements is done at Time Future. The RATIOs at Time Future and at Time Zero are then compared to ascertain the microbiological activity in the sample.

A modification of the methods of the fifth, sixth, seventh, eighth, ninth and tenth aspect of the instant claimed invention is possible. In this modification, measurements of the Fluorescent Signals in the respective Aliquots are made at Time Zero and at multiple Time Futures. The calculated Useful RATIOS are then plotted against the time at which each measurement used in the calculation of the Useful RATIO was done. The rate of change of the Useful RATIO with respect to time is used to ascertain and to monitor the extent of microbiological contamination in the opaque medium.

It is to be understood that for purposes of this patent application, the use of the term "plotted" or "plotting" refers to any acceptable method of determining the rate of change of RATIO relative to time and is not meant to require that any actual physical plotting of the information be done. Of course, actual plotting is one acceptable means of determining the rate of change, however, other acceptable means are using manual or automatic calculation techniques wherein the data may be displayed graphically or in tables or in some sort of array that indicates the relationship between RATIO and time and the rate of change of RATIO with time. In addition, it is also acceptable that plotting refers to simply determining the rate of change of RATIO with time wherein no actual intermediate steps are recorded.

In measuring the fluorescent signals at Time Future it is quite possible that some settling of the contents of each Aliquot may have occurred. This settling is normal. Prior to taking the measurements at Time Future it is recommended that each Aliquot be stirred to redistribute the contents of the Aliquot, throughout the Aliquot.

In the ninth and tenth aspect of the instant claimed invention an Aliquot of opaque medium is removed to which Nutrient is first added, followed by Fluorogenic Dye. This Aliquot is then referred to as Aliquot-Nutrient-Dye. By measuring the fluorescent signal of Aliquot-Nutrient-Dye it is possible to measure the TOTAL Microbiological Activity through its effect upon the Fluorogenic Dye. The TOTAL Microbiological Activity is a combination of the Active Microbiological Activity and the Inactive Microbiological Activity. The Active Microbiological Activity is that activity attributed to those microorganisms in an active state. The Inactive Microbiological Activity is that activity attributed to those microorganisms that are in a quiescent, or inactive state. The Inactive Microbiological activity is measured by added Nutrient to the Aliquot. The Nutrient acts as a food source for the Inactive Microorganisms, causing them to become Active.

The Nutrient can be any known material capable of supporting the growth of microorganisms. The Nutrient may be selected from the group consisting of carbohydrates, nutrient broth including proteins and other ingredients and mixtures thereof with water. Preferably the Nutrient is a solution of dextrose, nutrient broth and water. The amount of Nutrient added to the Aliquot is from about 10 ppm to about 10,000 ppm, preferably from about 100 ppm to about 2000 ppm and most preferably about 700 ppm.

A summary of some, but not all of the possible calculations of Useful RATIOs that can be of value in the method of the instant claimed invention, are given in the following paragraphs.

Abbreviations used in these calculations are as follows:

AB is the Fluorescent Signal in Aliquot-Blank.

AD is the Fluorescent Signal in Aliquot-Dye.

AID is the Fluorescent Signal in Aliquot-Inhibitor-Dye.

AND is the Fluorescent Signal in Aliquot-Nutrient-Dye.

FD refers to Fluorogenic Dye.

RFD refers to Reacted Fluorogenic Dye.

TZero refers to Time Zero.

TFuture refers to Time Future.

For the First Aspect of the Instant Claimed Invention, the Useful RATIO is;

$$\frac{AD^{RFD}}{AD^{FD}}$$

Described in words this Useful RATIO is the RATIO of the Fluorescent Signal of the Reacted Fluorogenic Dye in Aliquot-Dye to the Fluorescent Signal of the Fluorogenic Dye in Aliquot-Dye.

For the Third Aspect of the Instant Claimed Invention, a Useful RATIO is:

$$\frac{AD^{RFD} - AB^{RFD}}{AD^{FD} - AB^{FD}}$$

Described in words this Useful RATIO is the RATIO of the Fluorescent Signal of the Reacted Fluorogenic Dye in Aliquot Dye minus the Fluorescent Signal at the wavelength of the Reacted Fluorogenic Dye in Aliquot Blank to the Fluorescent Signal of the Fluorogenic Dye in Aliquot Dye minus the Fluorescent Signal at the wavelength of the Fluorogenic Dye in Aliquot Blank.

This Ratio is also referred to as the RATIO Adjusted for Background Fluorescence.

For the Fifth Aspect of the Instant Claimed Invention a Useful RATIO is the RATIO adjusted for interactions with chemicals and background fluorescence:

$$\frac{AD^{RFD} - AB^{RFD}}{AD^{FD} - AB^{FD}} - \frac{AID^{RFD} - AB^{RFD}}{AID^{FD} - AB^{FD}}$$

Another Useful RATIO is the RATIO for total activity (microbial+chemicals+background) over a timeperiod:

$$\frac{AD^{RFDatTFuture} - AB^{RFDatTZero}}{AD^{FDatTFuture} - AB^{FDatTZero}}$$

Another Useful RATIO is the RATIO adjusted for background fluorescence at Time Zero and at Time Future.

$$\frac{AD^{RFD\ at\ TFuture} - AB^{RFD}}{AD^{FD\ at\ TFuture} - AB^{FD}} - \frac{AD^{RFD\ at\ TZero} - AB^{RFD}}{AD^{FD\ at\ TZero} - AB^{FD}}$$

Note
$AB^{RFD\ at\ Time\ Future}$ can be $AB^{RFDatTZero}$ if no settling occurs, or if after agitation, the slurry returns to its pre-Time Future level of opacity.
$AB^{FD\ at\ Time\ Future}$ can be $AB^{FD\ at\ TZero}$ if no settling occurs, or if after agitation, the slurry returns to its pre-Time Future level of opacity Another Useful RATIO is the RATIO adjusted for background fluorescence and interactions with chemicals.

$$\frac{(AD^{RFDatTFuture} - AB^{RFD})}{(AD^{FDatTFuture} - AB^{FD})} - \frac{AID^{RFDatTFuture} - AB^{RFD})}{AID^{FDatTFuture} - AB^{FD})} -$$

$$\frac{(AD^{RFDatTZero} - AB^{RFD})}{(AD^{FDatTZero} - AB^{FD})} - \frac{AID^{RFDatTZero} - AB^{RFD})}{AID^{FDatTZero} - AB^{FD})} =$$

Active microbial activity only between Time Future and Time Zero.

Another Useful RATIO is the RATIO for total microbial activity corrected for background fluorescence and interactions with chemicals.

$$\frac{(AND^{RFDatTFuture} - AB^{RFD})}{(AND^{FD\ at\ TFuture} - AB^{FD})} - \frac{AID^{RFDatTFuture} - AB^{RFD})}{AID^{FD\ at\ TFuture} - AB^{FD})} -$$

$$\frac{(AND^{RFD\ at\ TZero} - AB^{RFD})}{(AND^{FD\ at\ TZero} - AB^{FD})} - \frac{AID^{RFD\ at\ TZero} - AB^{RFD})}{AID^{FD\ at\ TZero} - AB^{FD})} =$$

Total microbial activity only.

Another Useful RATIO is the RATIO for inactive microbial activity corrected for background fluorescence and interactions with chemicals which can be obtained by subtracting the RATIO of active microbial activity from RATIO for total microbial activity.

As is true for the first, second, third and fourth aspect of the instant claimed invention; in the fifth, sixth, seventh, eighth, ninth and tenth aspect of the instant claimed invention, the preferred Fluorogenic Dye is Resazurin. The most preferred Fluorogenic Dye is a solution of Resazurin in pH 8.0 phosphate buffer. This is the most preferred Fluorogenic Dye because the buffer helps to increase the sensitivity of the test by buffering up the pH of slightly acidic samples.

By conducting the methods of the instant claimed invention it is possible to monitor the microbiological contamination of an opaque medium and use the monitoring information to control the amount of biocide added to the opaque medium.

The following examples are presented to be illustrative of the present invention and to teach one of ordinary skill how to make and use the invention. These examples are not intended to limit the invention or its protection in any way.

EXAMPLES

Example 1

Fluorescent Properties of one Fluorogenic Dye and the Reacted Fluorogenic Dye in a Mineral Slurry Example 1a
Investigation of Fluorescent Signal Properties of Resazurin
Resazurin, sodium salt, is available from ALDRICH®. In aqueous slurries and colloids and certain Metal Working Fluids, the salt dissolves, leaving the Resazurin as a Fluorogenic Dye that can react with the respiratory enzyme, dehydrogenase, present in the membrane of many microbiological organisms. Because of this reaction with dehydrogenase, Resazurin is reduced to 3H-phenoxazin-3-one, 7-hydroxy-, also known as Resorufin. Resazurin and Resorufin have different fluorescent signals. Resazurin has a known fluorescent emission signal maximum at 634 nm while Resorufin has a known fluorescent emission signal maximum at 583 nm.

A plot of fluorescent signals (in counts per second) of Resazurin and Resorufin in a Mineral Slurry at Time Zero and at Time Future is shown in FIG. 1. The mineral slurry at Time Zero contained 25 ppm Resazurin. Time Zero in this Example is about one minute. Time Future is about 4 hours.

The spectra shown in FIG. 1 were obtained using a SPEX™ fluorometer available from Jobin Yvon SPEX, 3880 Park Avenue, Edison N.J. 08820. The fluorometer was set up as follows: Bandwidth was set at 2.5 nm for both excitation and emission, the excitation wavelength was set at 550 nm and the emission was scanned between 570 and 650 nm at 1 nm step intervals with 0.2 second integration time at each step. The SPEX™ fluorometer uses single photon counting so the readings are reported in counts per second.

In FIG. 1, the Time Zero spectrum is shown as the smooth line and the y-axis for the Time Zero spectrum is the secondary y-axis with units of from 0 to 200,000 counts per second. The Time Future spectrum in FIG. 1 is shown as the dotted line and the y-axis for the Time Future spectrum is the primary y-axis with units of from 0 to 2,000,000 counts per second. These two y-axes were chosen in order to fit the Time Future and Time Zero spectrum on the same Figure.

The Time Zero spectrum has peaks at both 583 nm and 634 nm, indicating the presence of small quantities of Resorufin present within the sample of Resazurin. The sample of Resazurin used had a small quantity of Resorufin present, which means this spectrum accurately reflected the composition of the sample at Time Zero. The 4-hour spectrum also has peaks at 583 nm and 634 nm but the relative intensity of these peaks are considerably different. The spectra, taken together indicate that from Time Zero to Time Future, Resazurin is being reduced to Resorufin, either by the action of microbiological organisms present in the mineral slurry or by the action of chemical induced reduction of Resazurin to Resorufin or by a combination of both of these actions.

The action of microbiological organisms reduces Resazurin because of the membrane-bound dehydrogenases present in microorganisms. Dehydrogenases are a class of electron transfer enzymes present in all microbiological organisms. Without the interaction with the microbiological organisms, Resazurin does not by itself, in real-time, convert to Resorufin, in the absence of chemical reducing agents.

The ongoing interaction with microbiological organisms causes the 583 nm peak to increase in intensity compared to the peak at 634 nm. By calculating the RATIO of the intensity of the 583 nm peak (Reacted Fluorogenic Dye peak) to the 634 nm peak (Fluorogenic Dye peak) the extent of microbiological activity and the presence of chemical reducing agents within the system can be determined.

Example 1b

Discussion of RATIO Limits

The calculated RATIO of the fluorescent signal of a Reacted Fluorogenic Dye to the fluorescent signal of the Fluorogenic Dye has limiting values. After interaction with the microbiological organisms the RATIO steadily increases. This increase continues proportionately with microbial activity until the value saturates. The value at which the RATIO saturates depends on the sensitivity and calibration of the fluorometer as well as on the choice of Fluorogenic Dye. When Resazurin is chosen as the Fluorogenic Dye and the SPEX™ fluorometer is used the calculated RATIO saturates at 5. When Resazurin is chosen as the Fluorogenic Dye and certain light emitting diode fluorometers are used, the calculated RATIO saturates at 6.

By saturates it is meant that this is the maximum measurable value of the RATIO. The microbial activity may continue unabated for a long period afterwards, but the value of the RATIO would not continue to increase. In fact, the RATIO will eventually decrease as Resorufin is further reduced to nonfluorescent dihydroresorufin.

The spectrum of Resorufin (pure) has a RATIO of 5 in its spectrum between the intensity at 583 nm and the intensity at 634 nm. Hence if the concentration of Resazurin is very small, Resorufin's spectrum dominates. This is because one molecule of Resorufin has a greater quantum yield of fluorescence compared to one molecule of Resazurin.

The reason for saturation is, believed to be, without intending to be bound thereby, based on the following: Resorufin has an emission maximum at 583 nm, however, it also emits slightly at 634 nm. The emission intensity at 634 nm is one-fifth the intensity at 583 nm. Resorufin is also a more fluorescent species than Resazurin (i.e. if equimolar amounts of Resazurin and Resorufin are excited at a particular wavelength, in this case 550 nm, the intensity of the fluorescence from Resorufin far exceeds that from Resazurin). As a result, when most of the Resazurin has been converted to Resorufin by the microbiological organisms, the fluorescence intensity RATIO saturates to the value for the Resorufin peak alone.

Procedure for Examples 2 and 3

Reagents

Fluorogenic Dye was a 1000 ppm solution of Resazurin in water, buffered to a pH of 8.0.

Nutrient was a 28,000 ppm solution of glucose and commercial Nutrient broth (from Becton Dickinson Microbiological Systems, Sparks Md., 21152 U.S.A. (410)-316-4000) in water.

Metabolic Inhibitor was a 200,000 ppm solution of pentachlorophenol in dipropylene glycol methyl ether.

Apparatus Needed

Pipettes and tips (to pipet 200 µL solutions)

Transfer pipettes

Standard disposable cuvettes 15 ml polystyrene centrifuge tubes with lids or any transparent tube with lids Front-Face Fluorometer Procedure (If the slurry is too thick to mix, dilute the slurry (initially before transferring) just enough to enable adequate mixing of slurry and reagents. This slurry should be used for blank measurement also.)

1. Transfer 8 ml of Aliquot of slurry into 15-ml centrifuge tube.
2. Add 0.2 ml of Nutrient to the tube and mark it "Aliquot-Nutrient-Dye"
3. Place lid on the tube and shake well to mix.
4. Transfer 8-ml of the same sample into another 15-ml centrifuge tube.
5. Add 0.2 ml of the Metabolic Inhibitor to this tube and mark it "Aliquot-Inhibitor-Dye".
6. Place lids on the tube and shake well to mix.
7. Follow this procedure by repeating steps 1 through 6 for "n" number of Aliquots.
8. Let tubes stand for 15 minutes.
9. Add 240 µL of Fluorogenic Dye to each tube.
10. Place lids on the tubes and shake well to mix.
11. Transfer about 4.0 ml of Aliquot from each tube into separate standard disposable cuvettes.
12. Measure fluorescence of Reacted Fluorogenic Dye and Fluorogenic Dye at about one minute. The Fluorogenic Dye and the Reacted Fluorogenic Dye are excited at 532 nm and the emitted peaks are measured at 634 nm and 583 nm respectively. Note down the readings. For e.g. fluorescence reading of Aliquot 1, Aliquot-Nutrient-Dye, should be noted under "Reacted Fluorogenic Dye, Aliquot-Nutrient-Dye at Time Zero" and "Fluorogenic Dye, Aliquot-Nutrient-Dye at Time Zero" respectively. The fluorescence reading of Aliquot 2, "Aliquot-Inhibitor-Dye" should be noted under "Reacted Fluorogenic Dye, Aliquot-Inhibitor-Dye at Time Zero" and "Fluorogenic Dye, Aliquot-Inhibitor-Dye at Time Zero" respectively.
13. Repeat Steps 11 and 12 for each set of aliquots.
14. Incubate the remaining aliquots in the centrifuge tubes at 37° C.
15. At Time Future, which is 6 hours after Time Zero, remove the tubes from the incubator. Transfer about 3 ml of each aliquot from tubes to another set of standard disposable cuvettes.
16. Measure fluorescence of Reacted Fluorogenic Dye and Fluorogenic Dye of each aliquot. Note down the readings. For e.g. fluorescence reading of Aliquot 1, Aliquot-Nutrient-Dye, should be noted under "Reacted Fluorogenic Dye, Aliquot-Nutrient-Dye at Time Future" and "Fluorogenic Dye, Aliquot-Nutrient-Dye at Time Future" respectively. The fluorescence reading of Aliquot 2, Aliquot-Inhibitor-Dye should be noted under "Reacted Fluorogenic Dye, Aliquot-Inhibitor-Dye at Time Future" and "Fluorogenic Dye, Aliquot-Inhibitor-Dye at Time Future" respectively.

17. Repeat Steps 15 and 16 for each set of aliquots.

Blank Measurement

18. Transfer 3 ml of the original sample to another set of standard disposable cuvettes. Mark them Aliquot-Blank for each aliquot.
19. Measure fluorescence of each aliquot at wavelengths of Reacted Fluorogenic Dye and Fluorogenic Dye. Note down the readings. For e.g. fluorescence reading of Aliquot 3 should be noted under "Reacted Fluorogenic Dye, Aliquot-Blank and Fluorogenic Dye, Aliquot-Blank" respectively.

Interpretation of Results

Calculated Total Microbiological Activity of <0.1 denotes low microbiological activity;

Calculated Total Microbiological Activity between 0.1 and 0.2 denotes medium microbiological activity;

Calculated Total Microbiological Activity of >0.2 denotes high microbiological activity.

Example 2

The opaque medium chosen for analysis was a coating from the Paper industry, containing clay, starch, calcium carbonate and a latex polymer.

Aliquot-Blank measurements of the Fluorescent Signals of the Fluorogenic Dye and the Reacted Fluorogenic Dye were taken once at Time Zero and the measurements were used for Aliquot-Blank for both Time Zero and Time Future.

Aliquot-Dye measurements of the Fluorescent Signals of the Fluorogenic Dye and the Reacted Fluorogenic Dye were taken at Time Zero. Aliquot-Blank measurements of the Fluorescent Signals of the Fluorogenic Dye and the Reacted Fluorogenic Dye were subtracted from Aliquot-Dye measurements of the Fluorescent Signals of the Fluorogenic Dye and the Reacted Fluorogenic Dye taken at Time Zero respectively. Useful RATIO of measurements of the Fluorescent Signals of the Reacted Fluorogenic Dye to Fluorogenic Dye of the Aliquot-Dye adjusted for the Aliquot-Blank measurements were calculated.

Aliquot-Inhibitor-Dye measurements of the Fluorescent Signals of the Fluorogenic Dye and the Reacted Fluorogenic Dye were taken at Time Zero. Aliquot-Blank measurements of the Fluorescent Signals of the Fluorogenic Dye and the Reacted Fluorogenic Dye were subtracted from Aliquot-Inhibitor-Dye measurements of the Fluorescent Signals of the Fluorogenic Dye and the Reacted Fluorogenic Dye taken at Time Zero respectively. Useful RATIO of measurements of the Fluorescent Signals of the Reacted Fluorogenic Dye to Fluorogenic Dye of the Aliquot-Inhibitor-Dye adjusted for the Aliquot-Blank measurements were calculated.

Aliquot-Nutrient-Dye measurements of the Fluorescent Signals of the Fluorogenic Dye and the Reacted Fluorogenic Dye were taken at Time Zero. Aliquot-Blank measurements of the Fluorescent Signals of the Fluorogenic Dye and the Reacted Fluorogenic Dye were subtracted from Aliquot-Nutrient-Dye measurements of the Fluorescent Signals of the Fluorogenic Dye and the Reacted Fluorogenic Dye taken at Time Zero respectively. Useful RATIO of measurements of the Fluorescent Signals of the Reacted Fluorogenic Dye to Fluorogenic Dye of the Aliquot-Nutrient-Dye adjusted for the Aliquot-Blank measurements were calculated.

Similar measurements of the Fluorescent Signals of the Reacted Fluorogenic Dye and Fluorogenic Dye in Aliquot-Dye, Aliquot-Inhibitor-Dye and Aliquot-Nutrient-Dye were taken at Time Future, adjusted for Aliquot-Blank measurements and the Useful RATIOs were calculated. Time Future was six hours after Time Zero.

| Sample Description | Aliquot Dye: Useful RATIO of Reacted Fluorogenic Dye to Fluorogenic Dye | | Aliquot-Inhibitor-Dye: Useful RATIO of Reacted Fluorogenic Dye to Fluorogenic Dye | | Aliquot-Nutrient-Dye: Useful RATIO of Reacted Fluorogenic Dye to Fluorogenic Dye | |
|---|---|---|---|---|---|---|
| | Time Zero | Time Future | Time Zero | Time Future | Time Zero | Time Future |
| Coating from Paper industry, consisting of clay, starch, calcium carbonate, latex polymer | 0.279 | 0.565 | 0.126 | 0.356 | 0.259 | 0.52 |
| | Total Activity without Nutrient: Time Future − Time Zero 0.565 − 0.279 = 0.286 | | Chemical Interference: Time Future − Time Zero 0.356 − 0.126 = 0.230 | | Total Activity with Nutrient: Time Future − Time Zero 0.52 − 0.259 = 0.261 | |

Total Activity without Nutrient = Active Microbiological + Chemical Interference;
Total Activity with Nutrient = Active Microbiological + Inactive Microbiological + Chemical Interference;
Total Microbiological = Total Activity with Nutrient − Chemical Interference = 0.261 − 0.230 = 0.031;
Active Microbiological = Total Activity without Nutrient − Chemical Interference = 0.286 − 0.230 = 0.056
Inactive Microbiological = Total Microbiological − Active Microbiological = 0.031 − 0.056 = −0.025; this number is indicative of the absence of Inactive Microbiological.

Total Microbiological Activity of 0.031 denotes very low microbiological activity corresponding to a low density of 1000 colony forming units per milliliter of sample (determined by standard plate count activity).

The numbers representing Total Microbiological and Active Microbiological of 0.031 and 0.056 respectively, are so close together that the difference between them is negligible.

The sample originally showed high Total Activity with and without Nutrients and high Chemical Interference. Chemical Interference subtracted from Total Activity with Nutrients yielded low Total Microbiological, corresponding to low plate counts.

Example 3

The opaque medium chosen for analysis was an uncooked starch slurry from the paper industry.

Aliquot-Blank measurements of the Fluorescent Signals of the Fluorogenic Dye and the Reacted Fluorogenic Dye were taken once at Time Zero and these measurements were used for Aliquot-Blank for both Time Zero and Time Future.

Aliquot-Inhibitor-Dye measurements of the Fluorescent Signals of the Fluorogenic Dye and the Reacted Fluorogenic Dye were taken at Time Zero. Aliquot-Blank measurements of the Fluorescent Signals of the Fluorogenic Dye and the Reacted Fluorogenic Dye were subtracted from Aliquot-Inhibitor-Dye measurements of the Fluorescent Signals of the Fluorogenic Dye and the Reacted Fluorogenic Dye taken at Time Zero respectively. Useful RATIO of measurements of the Fluorescent Signals of the Reacted Fluorogenic Dye to Fluorogenic Dye of the Aliquot-Inhibitor-Dye adjusted for the Aliquot-Blank measurements were calculated.

Aliquot-Nutrient-Dye measurements of the Fluorescent Signals of the Fluorogenic Dye and the Reacted Fluorogenic Dye were taken at Time Zero. Aliquot-Blank measurements of the Fluorescent Signals of the Fluorogenic Dye and the Reacted Fluorogenic Dye were subtracted from Aliquot-Nutrient-Dye measurements of the Fluorescent Signals of the Fluorogenic Dye and the Reacted Fluorogenic Dye taken at Time Zero respectively. Useful RATIO of measurements of the Fluorescent Signals of the Reacted Fluorogenic Dye to Fluorogenic Dye of the Aliquot-Nutrient-Dye adjusted for the Aliquot-Blank measurements were calculated.

Similar measurements of the Fluorescent Signals of the Reacted Fluorogenic Dye and Fluorogenic Dye in Aliquot-Dye, Aliquot-Inhibitor-Dye and Aliquot-Nutrient-Dye were taken at Time Future, adjusted for Aliquot-Blank measurements and the Useful RATIOs were calculated. Time Future was six hours after Time Zero.

| Sample Description | Aliquot-Inhibitor-Dye: Useful RATIO of Reacted Fluorogenic Dye to Fluorogenic Dye | | Aliquot-Nutrient-Dye: Useful RATIO of Reacted Fluorogenic Dye to Fluorogenic Dye | |
|---|---|---|---|---|
| Uncooked starch slurry from the paper industry | Time Zero 0.186 | Time Future 0.225 | Time Zero 0.167 | Time Future 0.781 |
| | Chemical Interference: Time Future − Time Zero 0.225 − 0.186 = 0.039 | | Total Activity: Time Future − Time Zero 0.781 − 0.167 = 0.614 | |

Total Activity = Total Microbiological + Chemical Interference = 0.614
Total Microbiological = Total Activity − Chemical Interference = 0.614 − 0.039 = 0.575

Bacterial Counts were determined by standard plate counting methods to be about 56,000,000 colony forming units per milliliter of sample.

The sample originally showed high Total Activity and low Chemical Interference. Chemical Interference subtracted from Total Activity yielded high Total Microbiological, corresponding to high plate counts.

Changes can be made in the composition, operation and arrangement of the method of the instant claimed invention described herein without departing from the concept and scope of the invention as defined in the following claims:

What is claimed is:

1. A process for monitoring of microbiological populations in an opaque medium comprising:
   (a) obtaining an Aliquot of material from the opaque medium;
   (b) adding a Fluorogenic Dye to said Aliquot, wherein said Aliquot is now referred to as Aliquot-Dye;
   (c) allowing said Fluorogenic Dye to react with any microbiological organisms present;
   (d) providing means for measurement of the fluorescent signals of the Fluorogenic Dye and the Reacted Fluorogenic Dye in said Aliquot-Dye;
   (e) using said means for measurement to measure the fluorescent signals of the Fluorogenic Dye and the Reacted Fluorogenic Dye, while discarding any measured fluorescent signal values below a predetermined noise level;
   (f) calculating the RATIO of the fluorescent signal of the Reacted Fluorogenic Dye to the fluorescent signal of the Fluorogenic Dye; and
   (g) using said RATIO to monitor the extent of microbiological contamination in said opaque medium.

2. The process of claim 1 further comprising:
   (h) using said RATIO to determine the optimal amount of biocide to deliver to the opaque medium; and
   (i) delivering said optimal amount of biocide to the opaque medium.

3. A process for monitoring of microbiological populations in an opaque medium comprising:
   (A) separating at least two Aliquots of material, optionally three Aliquots of material, from the opaque medium;
   (B) adding nothing to the first Aliquot, wherein said first Aliquot is now referred to as Aliquot-Blank, adding a Fluorogenic Dye to the second Aliquot, wherein said second Aliquot is now referred to as Aliquot-Dye, and when the optional third Aliquot is present, adding a Metabolic Inhibitor to the optional third Aliquot, followed by adding Fluorogenic Dye to the optional third Aliquot, wherein said third Aliquot is now referred to as optional Aliquot-Inhibitor-Dye;
   (C) allowing said Fluorogenic Dye to react with any microbiological organisms present;
   (D) providing means for measurement of the fluorescent signals in said Aliquot-Blank, in said Aliquot-Dye, and in said optional Aliquot-Inhibitor-Dye, with the fluorescent signals being measured at the wavelength of the Fluorogenic Dye and at the wavelength of the Reacted Fluorogenic Dye;
   (E) using said means for measurement of said fluorescent signals to measure the fluorescent signals in Aliquot-Blank, Aliquot-Dye, and in optional Aliquot-Inhibitor-Dye, at the wavelength of the Fluorogenic Dye and at the wavelength of the Reacted Fluorogenic Dye, while discarding any measured fluorescent signal values below a predetermined noise level;
   (F) calculating the Useful RATIO, wherein the Useful RATIO is selected from the group consisting of RATIO of Adjusted for Background Fluorescence Fluorescent Signal of the Reacted Fluorogenic Dye to the Adjusted for Background Fluorescence Fluorescent Signal of the Fluorogenic Dye and RATIO of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye;
   (G) using the Useful RATIO to monitor the extent of microbiological contamination in said opaque medium.

4. The process of claim 3 further comprising:
   (H) using one or both of the Useful RATIOs from steps (F) and (G) to determine the optimal amount of biocide to deliver to said opaque medium; and (I) delivering said optimal amount of biocide to the opaque medium.

5. A process for monitoring of microbiological populations in an opaque medium comprising:
   a) obtaining an Aliquot of material from the opaque medium;
   b) adding a Fluorogenic Dye into said Aliquot, wherein said Aliquot is now referred to as Aliquot-Dye;
   c) allowing said Fluorogenic Dye to react with any microbiological organisms present for a time period known as Time Zero;
   d) providing means for measurement of the fluorescent signals of the Fluorogenic Dye and the Reacted Fluorogenic Dye in said Aliquot-Dye;
   e) using said means for measurement of said fluorescent signals to measure the fluorescent signals of the Fluorogenic Dye and the Reacted Fluorogenic Dye at Time Zero, while discarding any measured fluorescent signals values below a predetermined noise level;
   f) calculating the RATIO of the fluorescent signal of the Reacted Fluorogenic Dye to the fluorescent signal of the Fluorogenic Dye and designating that RATIO the RATIO at Time Zero;
   g) waiting for a time period, designated Time Future;
   h) measuring the fluorescent signals of the Fluorogenic Dye and the Reacted Fluorogenic Dye in Aliquot-Dye at Time Future;
   i) calculating the RATIO of the fluorescent signal of the Reacted Fluorogenic Dye at Time Future to the fluorescent signal of the Fluorogenic Dye at Time Future, designating that RATIO the RATIO at Time Future;
   j) comparing the RATIO at Time Future to the RATIO at Time Zero;
   k) using the comparison of the RATIO at Time Future to the RATIO at Time Zero to monitor the extent of microbiological contamination in said opaque medium.

6. The process of claim 5 further comprising:
   l) using the comparison of the RATIO at Time Future to the RATIO at Time Zero to determine the optimal amount of biocide to deliver to said opaque medium; and
   m) delivering said optimal amount of biocide to the opaque medium.

7. A process for monitoring of microbiological populations in an opaque medium comprising:
   (A) separating at least two Aliquots of material, optionally three Aliquots of material, from the opaque medium;
   (B) adding nothing to the first Aliquot, wherein said first Aliquot is now referred to as Aliquot-Blank, adding a Fluorogenic Dye to the second Aliquot, wherein said second Aliquot is now referred to as Aliquot-Dye, and when the optional third Aliquot is present, adding a Metabolic Inhibitor followed by a Fluorogenic Dye to the optional third Aliquot, wherein the optional third Aliquot is now referred to as optional Aliquot-Inhibitor-Dye;
   (C) allowing said Fluorogenic Dye to react with any microbiological organisms present for a time period known as Time Zero;
   (D) providing means for measurement of the fluorescent signals in said Aliquot-Blank, in said Aliquot-Dye and in said optional Aliquot-Inhibitor-Dye, with the fluorescent signals being measured at the wavelength of the Fluorogenic Dye and at the wavelength of the Reacted Fluorogenic Dye;
   (E) using said means for measurement of said fluorescent signals to measure the fluorescent signals in Aliquot-Blank, Aliquot-Dye and in optional Aliquot-Inhibitor-Dye at Time Zero, at the wavelength of the Fluorogenic Dye and the wavelength of the Reacted Fluorogenic Dye, while discarding any measured fluorescent signal values below a predetermined noise level to yield fluorescent signals at Time Zero;
   (F) calculating the Useful RATIO at Time Zero, wherein the Useful RATIO at Time Zero is selected from the group consisting of RATIO at Time Zero of the Adjusted for Background Fluorescence Fluorescent Signal of the Reacted Fluorogenic Dye to the Adjusted for Background Fluorescence Fluorescent Signal of the Fluorogenic Dye at Time Zero and optional RATIO of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye;
   (G) waiting for a time period, designated Time Future;
   (H) using said means for measurement to measure the fluorescent signals at Time Future in Aliquot-Blank, Aliquot-Dye and in optional Aliquot-Inhibitor-Dye at the wavelength of the Fluorogenic Dye and the wavelength of the Reacted Fluorogenic Dye;
   (I) calculating the Useful RATIO at Time Future, wherein the Useful RATIO at Time Future is selected from the group consisting of RATIO at Time Future of the Adjusted for Background Fluorescence Fluorescent Signal of the Reacted Fluorogenic Dye to the Adjusted for Background Fluorescence Fluorescent Signal of the Fluorogenic Dye at Time Future and optional RATIO at Time Future of the Adjusted for Interactions with chemicals and Background Fluorescence Fluorescent Signal of the Reacted Fluorogenic Dye to the Adjusted for Interactions with chemicals and Background Fluorescence Fluorescent Signal of the Fluorogenic Dye;
   (J) comparing the Useful RATIO at Time Future to the RATIO at Time Zero; and
   (K) using the comparison of the Useful RATIO at Time Future to the RATIO at Time Zero to monitor the extent of microbiological contamination in said opaque medium.

8. The process of claim 7 further comprising:
   (L) using the comparison of the Useful RATIO at Time Future to the Useful RATIO at Time Zero to determine the optimal amount of biocide to deliver to said opaque medium; and
   (M) delivering said optimal amount of biocide to the opaque medium.

9. A process for monitoring both active and inactive microbiological populations in an opaque medium, optionally accounting for chemical interference with the test method, as well as optionally accounting for background fluorescence comprising:
   (A) obtaining two Aliquots of material, optionally three or four Aliquots of material from the opaque medium;
   (B) adding a Fluorogenic Dye directly into the first Aliquot, wherein the first Aliquot is now referred to as Aliquot-Dye, adding Nutrient and Fluorogenic Dye to the second Aliquot, wherein the second Aliquot is now referred to as Aliquot-Nutrient-Dye, when the optional third Aliquot is present, adding a Metabolic Inhibitor and Fluorogenic Dye to the optional third Aliquot, wherein the optional third Aliquot is now referred to as optional Aliquot-Inhibitor-Dye, and when the optional fourth Aliquot is present, adding nothing to the fourth Aliquot, wherein the fourth Aliquot is now referred to as optional Aliquot-Blank;

(C) allowing said Fluorogenic Dye to react with any microbiological organisms present for a time period known as Time Zero;

(D) providing means for measurement of the fluorescent signals in said Aliquot-Dye, said Aliquot-Nutrient-Dye, said optional Aliquot-Inhibitor-Dye and in said optional Aliquot-Blank, with the fluorescent signals in each Aliquot being measured at the wavelength of the Fluorogenic Dye and the wavelength of the Reacted Fluorogenic Dye;

(E) using said means for measurement of said fluorescent signals to measure the fluorescent signals at Time Zero in said Aliquot-Dye, said Aliquot-Nutrient-Dye, said optional Aliquot-Inhibitor-Dye and in said optional Aliquot-Blank, at the wavelength of the Fluorogenic Dye and at the wavelength of the Reacted Fluorogenic Dye to yield fluorescent signals at Time Zero;

(F) calculating the Useful RATIO at Time Zero, wherein the Useful RATIO at Time Zero can be selected from the group consisting of RATIO at Time Zero of the Total Microbiological, Optionally Accounting for Interactions with chemicals and Optionally Accounting for Background Interferences Fluorescent Signal of the Reacted Fluorogenic Dye to the Total Microbiological, Optionally Accounting for Interactions with chemicals and Optionally Accounting for Background Interferences, Fluorescent Signal of the Fluorogenic Dye, the RATIO at Time Zero of the Active Microbiological Fluorescent Signal of the Reacted Fluorogenic Dye to the Active Microbiological Fluorescent Signal of the Fluorogenic Dye and the RATIO at Time Zero of the Inactive Microbiological Fluorescent Signal of the Reacted Fluorescent Dye to the Inactive Microbiological Fluorescent Signal of the Fluorogenic Dye;

(G) waiting for a time period, designated Time Future, and measuring the fluorescent signals in said Aliquot-Dye, said Optional Aliquot-Inhibitor-Dye, said Aliquot-Nutrient-Dye and said optional Aliquot-Blank at the wavelength of the Fluorogenic Dye and the Reacted Fluorogenic Dye at Time Future;

(H) calculating the Useful RATIO at Time Future, wherein the Useful RATIO at Time Future is selected from the group consisting of RATIO at Time Future of the Total Microbiological, Optionally Accounting for Interactions with chemicals and Optionally Accounting for Background Interferences Fluorescent Signal of the Reacted Fluorogenic Dye to the Total Microbiological, Optionally Accounting for Interactions with chemicals and Optionally Accounting for Background Interferences, Fluorescent Signal of the Fluorogenic Dye, the RATIO at Time Future of the Active Microbiological Fluorescent Signal of the Reacted Fluorogenic Dye to the Active Microbiological Fluorescent Signal of the Fluorogenic Dye and the RATIO at Time Future of the Inactive Microbiological Fluorescent Signal of the Reacted Fluorescent Dye to the Inactive Microbiological Fluorescent Signal of the Fluorogenic Dye;

(I) comparing the Useful RATIO at Time Future to the Useful RATIO at Time Zero; and (J) using the comparison of the Useful RATIO at Time Future to the Useful RATIO at Time Zero to monitor the extent of microbiological contamination in said opaque medium.

10. The process of claim 9 further comprising:

(K) using said comparison of the Useful RATIO at Time Future to the Useful RATIO at Time Zero to determine the optimal amount of biocide to deliver to said opaque medium; and (L) delivering said optimal amount of biocide to the opaque medium.

11. The process of claim 7 wherein the detected fluorescent signals in Aliquot-Blank at Time Zero is used for both Time Zero and Time Future.

12. The process of claim 9 wherein the detected fluorescent signals in Aliquot-Blank at Time Zero is used for both Time Zero and Time Future.

13. The process of claim 1 in which said fluorogenic Dye is Resazurin.

14. The process of claim 3 in which said Fluorogenic Dye is Resazurin.

15. The process of claim 5 in which said Fluorogenic Dye is Resazurin.

16. The process of claim 7 in which said Fluorogenic Dye is Resazurin.

17. The process of claim 9 in which said Fluorogenic Dye is Resazurin.

18. The process of claim 1 in which said means for measurement of the fluorescent signals is a Front-Face Fluorometer.

19. The process of claim 7 in which said means for measurement of the fluorescent signals is a Front-Face Fluorometer.

20. The process of claim 9 in which said means for measurement of the fluorescent signals is a Front-Face Fluorometer.

21. The process of claim 5 further comprising:

(l) repeating steps g) through j); and (m) plotting the value for RATIO against the time that each RATIO was calculated at and using the rate of change of the RATIO with time to monitor the extent of microbiological contamination in said opaque medium.

22. The process of claim 21 further comprising:

(n) using the rate of change of the RATIO with time to determine the optimal amount of biocide to deliver to said opaque medium; and (o) delivering said optimal amount of biocide to the opaque medium.

23. The process of claim 7 further comprising:

(L) repeating steps (G) through (J); and (M) plotting the value for Useful RATIO against the time that each Useful RATIO was calculated at and using the rate of change of the Useful RATIO with time to monitor the extent of microbiological contamination in said opaque medium.

24. The process of claim 23 further comprising:

(N) using the rate of change of the RATIO with time to determine the optimal amount of biocide to deliver to said opaque medium; and (O) delivering said optimal amount of biocide to the opaque medium.

25. The process of claim 9 further comprising:

(K) repeating steps (G) through (J); and (L) plotting the value for Useful RATIO against the time that each Useful RATIO was calculated at and using the rate of change of the Useful RATIO with time to monitor the extent of microbiological contamination in said opaque medium.

26. The process of claim 25 further comprising:

(M) using the rate of change of the RATIO with time to determine the optimal amount of biocide to deliver to said opaque medium; and (N) delivering said optimal amount of biocide to the opaque medium.

* * * * *